(12) United States Patent
Jenkins

(10) Patent No.: US 7,377,188 B2
(45) Date of Patent: May 27, 2008

(54) SYSTEM FOR THE DETECTION OF TRACE VAPORS AND PARTICLES IN AIR

(75) Inventor: Anthony Jenkins, 47 Spruce Rd., North Reading, MA (US) 01864

(73) Assignee: Anthony Jenkins, North Reading, MA (US)

( * ) Notice: Subject to any disclaimer, the term of this patent is extended or adjusted under 35 U.S.C. 154(b) by 0 days.

(21) Appl. No.: 11/402,224

(22) Filed: Apr. 11, 2006

(65) Prior Publication Data

US 2006/0272393 A1 Dec. 7, 2006

Related U.S. Application Data

(60) Provisional application No. 60/670,189, filed on Apr. 11, 2005.

(51) Int. Cl.
*G01N 1/22* (2006.01)
(52) U.S. Cl. .................................................. 73/863.23
(58) Field of Classification Search ............. 73/863.23
See application file for complete search history.

(56) References Cited

U.S. PATENT DOCUMENTS

| | | | |
|---|---|---|---|
| 4,551,624 A * | 11/1985 | Spangler et al. ............. 250/287 |
| 5,200,614 A | 4/1993 | Jenkins | |
| 5,405,781 A * | 4/1995 | Davies et al. .................. 436/52 |
| 5,491,337 A | 2/1996 | Jenkins et al. | |
| 5,760,314 A | 6/1998 | Bromberg et al. | |
| 6,073,499 A | 6/2000 | Settles et al. | |
| 6,642,513 B1 | 11/2003 | Jenkins et al. | |
| 6,690,005 B2 | 2/2004 | Jenkins et al. | |
| 6,708,572 B2 | 3/2004 | Jenkins et al. | |
| 6,765,198 B2 | 7/2004 | Jenkins et al. | |
| RE38,797 E * | 9/2005 | Linker et al. ............. 73/863.12 |
| 6,945,127 B2 * | 9/2005 | Van Netten ............... 73/863.23 |
| 6,964,190 B2 * | 11/2005 | Shinohara et al. ......... 73/28.04 |
| 7,155,988 B2 * | 1/2007 | Cole et al. ................ 73/863.22 |
| 2002/0078767 A1 | 6/2002 | Jenkins et al. | |

FOREIGN PATENT DOCUMENTS

JP 10-314521 * 12/1998

OTHER PUBLICATIONS

English language abstract for JP10-314521.*
International Search Report of PCT/US2006/013396 dated Aug. 22, 2006.

* cited by examiner

*Primary Examiner*—Michael Cygan
(74) *Attorney, Agent, or Firm*—Lowrie, Lando & Anastasi, LLP

(57) ABSTRACT

A detector for the detection for trace vapors and particles in the air that includes a housing; a well formed in the housing; a heated filter positioned across the well; a source delivering sampled air substantially perpendicular to the open end of the well on a first side of the filter; a source to supply dry air across the first side of the filter; a detector line in communication with the at least one well on a second side of the filter; and a second dry air source for supplying air to the second side of the filter at a pressure below atmospheric pressure. An automatic inspection station that includes a vibrator for vibrating articles to be inspected. An automatic inspection station that includes a heating element positioned below an upper surface of the floor and an inlet positioned above the floor.

11 Claims, 7 Drawing Sheets

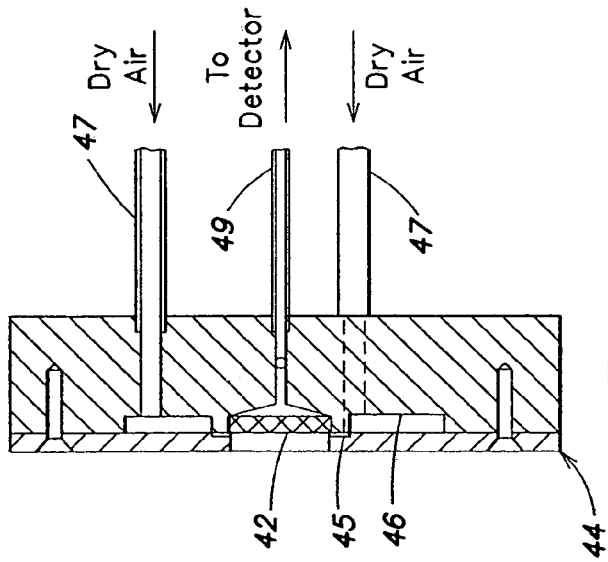
FIG. 4C
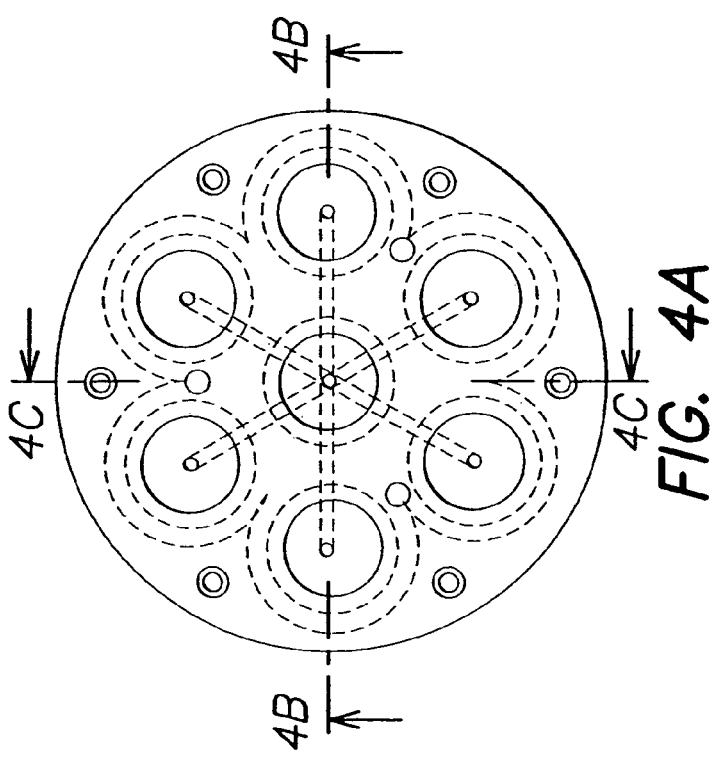
FIG. 4A
FIG. 4B

SYSTEM FOR THE DETECTION OF TRACE VAPORS AND PARTICLES IN AIR

RELATED APPLICATION

This application claims priority under 35 U.S.C. §119(e) to U.S. Provisional Application Ser. No. 60/670,189, entitled "IMPROVED SYSTEM FOR THE DETECTION OF TRACE VAPORS AND PARTICLES IN," filed on Apr. 11, 2005, which is herein incorporated by reference in its entirety.

FIELD OF INVENTION

The subject invention relates to detection systems for the detection of trace vapors and particles in air. It is particularly directed to the detection of traces of contraband materials such as explosives and illicit drugs.

DISCUSSION OF RELATED ART

The recent increased threat to society from improvised explosive devices (IEDs) and illicit drug traffic has lead to the development of extremely sensitive systems for the detection of traces of vapors and particles from explosives and drugs. GE Security and Smiths Detection market such systems, for example. Examples of prior art are described in U.S. Pat. Nos. 5,491,337; 6,708,572 and 6,642,513. Equipment is available for hand search, desktop operation and walkthrough portal security applications.

One prior art system, described in U.S. Pat. No. 5,491,337, draws air from the vicinity of a suspect package or person and detects the target vapors in an ion mobility detector. This detector cannot tolerate water vapor concentrations such as commonly exist in the atmosphere. Consequently, a dimethyl silicone membrane was deployed to largely prevent the passage of water vapor and other atmospheric contaminants while allowing the passage of at least a portion of the target vapors. Unfortunately the silicone membrane allows less than 10% of the sample vapor through to the detector. Furthermore, the membrane does not readily capture particles and many particles such as marijuana leaf particles pass through the system without being detected.

Prior art detection systems rely on the fact that trace amounts of contraband will be transferred to the body of a person who had handled the contraband and subsequently will be transferred from the body to any article the person may be carrying (e.g., handbag or suitcase). Trace amounts of contraband have been collected for analysis by wiping a small paper or fabric sample pad across the handbag or suitcase with or without the aid of a vacuum pump. The prior art sample pad then is inserted into a detection apparatus where the pad is heated to evaporate any particles and condensed vapors. The liberated vapor then is carried into the detector that is capable of detecting and identifying the target vapor.

Figure 1:
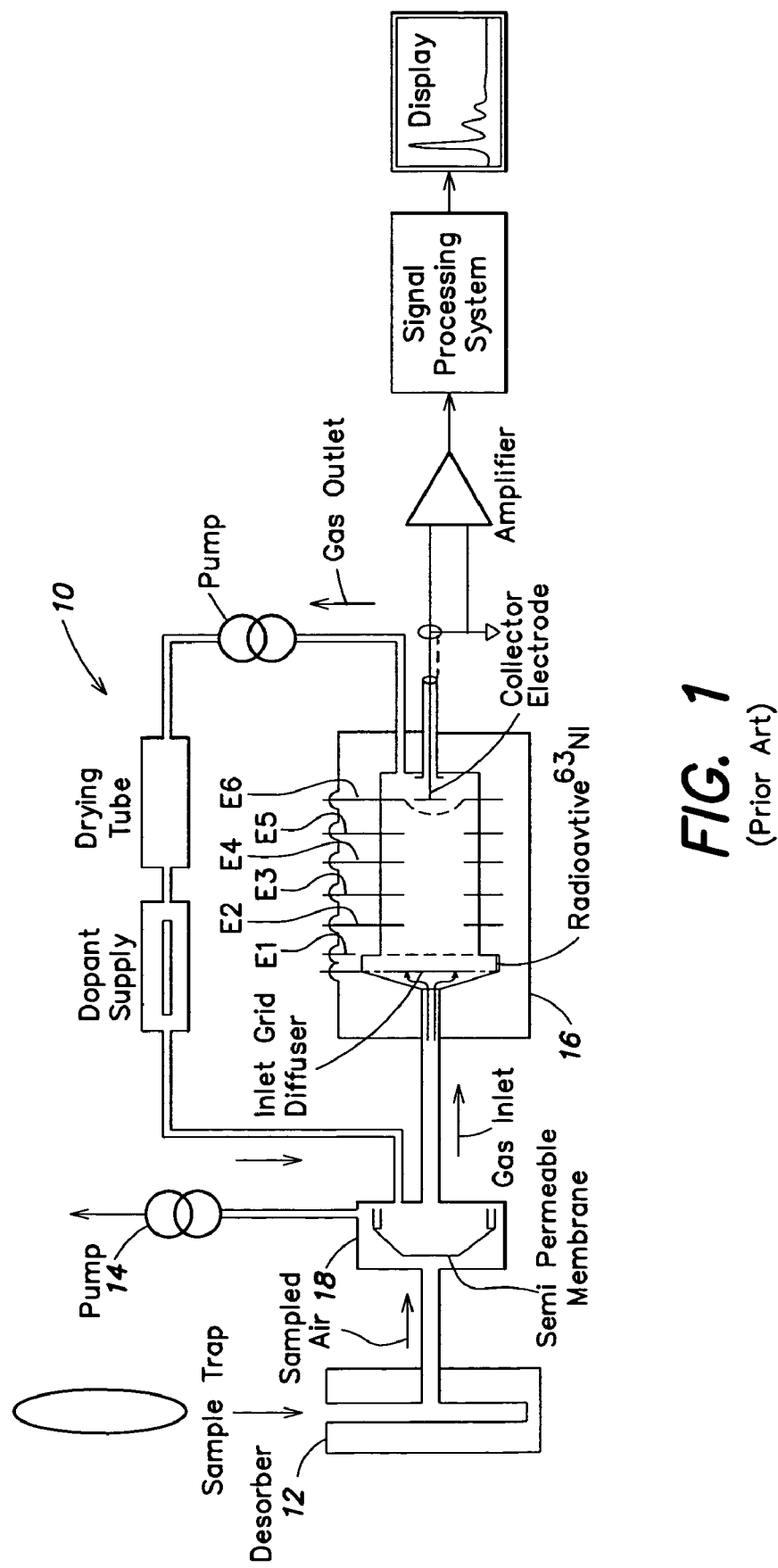

An existing system is illustrated schematically in FIG. 1. This prior art system of FIG. 1 is similar to the system described in greater detail in the above referenced U.S. Pat. No. 5,491,337. The prior art system of FIG. 1 analyzes samples that are collected on sample wipes consisting of a clean porous filter paper. These wipes are dropped into a thermal desorber, 12, in FIG. 1. Desorbed material is carried into the detector by the action of a sampling pump, 14. The sample air is drawn into the detector, 16, over a dimethyl silicone membrane, 18. Organic vapors diffuse through the semi permeable membrane and are carried into the detector on a stream of dry air. The detector may be an Ion Mobility Spectrometer (IMS) or an Ion Trap Mobility Spectrometer (ITMS). The dimethyl silicone membrane prevents all dust, dirt, and most of the atmospheric water vapor and oxides of nitrogen from reaching the detector. Unfortunately, the membrane, 18, is only a few percent efficient at transferring the materials of interest and this limits the ultimate sensitivity of the apparatus.

In view of the above, it is an object of the subject invention to provide a detection system that detects trace amounts of both vapors and particles from target materials without the necessity of employing sample traps to acquire the sample. This enables automatic testing of both people and baggage without human intervention in the sampling process.

It is a further object of the subject invention to increase the sensitivity of the detection system by allowing a greater proportion of the target material to reach the detector. This has the effect of increasing sensitivity and enables the extremely low volatility materials such as the plastic explosives to be detected by their vapor emissions. This also reduces the need to detect particulate contamination that may be present from previous contact or from secondary, innocent transfer. Vapor emissions are more indicative of the presence of contraband than is the presence of particulate material. It is therefore a further objective of the subject invention to differentiate whether a response is from vapors or particles.

The subject invention will find use in hand held sniffers and fixed installation portal and baggage inspection systems for the detection of contraband material. It is a further feature of the subject invention that continuous real time detection is achieved. This increases the speed of the detection process, and hence throughput of test articles or people, which in turn reduces the cost of the inspection and inconvenience.

U.S. Pat. No. 6,073,499 discloses a portal detection system that relies on the natural thermal plume generated in proximity to the human body to carry particles and vapors into a detector system mounted above the head of the subject under inspection. This method proved to be an improvement over previous sampling systems that relied on induced air curtains to carry the target vapors and particles into the detector. However, the human plume begins at knee level and is comparatively slow until it reaches mid torso when flow velocities approaching a meter per second are achieved. It is a further feature of the subject invention to provide faster transport of trace materials into a detector system without diluting the sample available.

SUMMARY OF INVENTION

The subject invention is directed to the sample acquisition and efficient transfer to a known detector such as an Ion Mobility Spectrometer or an Ion Trap Mobility Spectrometer (see U.S. Pat. Nos. 5,200,614; 6,765,198; and 6,690,005) or other detector commonly used for detection of trace organic materials. The subject invention is used in a similar configuration to that described in the above prior art and shown in FIG. 1. A major improvement in the subject invention is provided by replacing the dimethyl silicone membrane with a micro porous filter element, 21 shown in FIG. 2.

Figure 3:
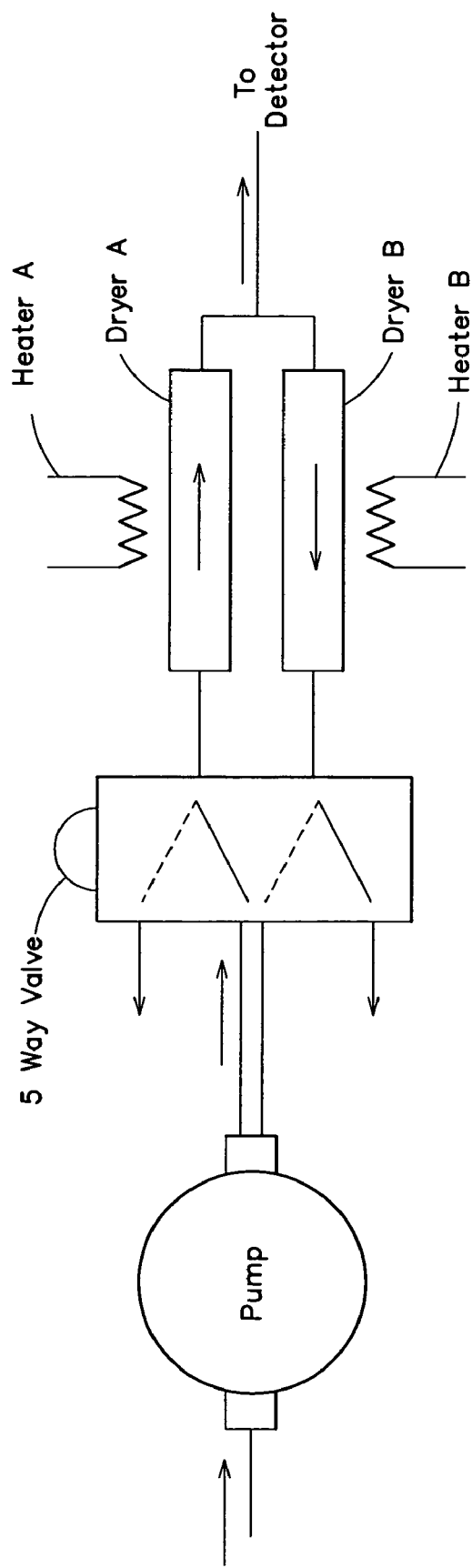

A second aspect of the subject invention also addresses improvement of the efficiency of the sampling process by providing a curtain of warm air through which the object or person is caused to pass. The warm air plume is applied at floor level and is arranged to be less than the natural human thermal plume that exists at shoulder level. Vapors and particles released into this warm air curtain are carried upwards into the detection system inlet. The temperature and flowrate of the warm air plume is controlled so that it is not additive to the human plume, but reduces the transport time from shoe level. In a baggage inspection station, the warm air plume carries trace materials from the baggage to a detector in much the same way as the human body plume in the portal inspection system.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 is a prior art detection system;

FIG. 2 is a schematic drawing of a detection system according to one embodiment of the invention;

FIG. 3 is a is a partial schematic drawing of a detection system according to one embodiment of the invention;

FIG. 4A is a front view of a filter manifold according to one embodiment of the invention;

FIG. 4B is a lower sectional view of the manifold of FIG. 4A;

FIG. 4C is a side sectional view of the manifold of FIG. 4A;

FIG. 5 is a stamping tool for use in connection with a detection system according to one embodiment of the invention;

FIG. 6 is a partial perspective view of an automatic inspection station according to one embodiment of the invention; and FIG. 7 is a schematic view of another automatic inspection station according to one embodiment of the invention.

DETAILED DESCRIPTION OF PREFERRED EMBODIMENT FOR LOW SAMPLE FLOWS

Sampled air is drawn in through an inlet tube, 22, shown in FIG. 2, by the action of a pump, 23. In order to prevent damp air being drawn into the detector, the subject invention incorporates a clean dry air supply that is arranged to flood the inlet side of the porous filter element, 21. Sampled air passing down the inlet tube, 22, impinges on the porous filter element and turns back through the concentric tube, 24, before continuing on to the pump, 23. The impinging sampled air would normally produce a boundary layer of stagnant air close to the surface of the porous filter, 21. Dry air is injected into this boundary region through an array of jets, 25, arranged in a ring at the surface of the filter element, 21. This dry air is drawn through the filter element, 21, by the action of a pump, 26. The pressure drop across the filter element, 21, is arranged to be sufficiently small that only a very small flow is induced through the filter element, and the boundary layer is not totally removed. The air passing through the filter element, 21, is drawn through the detector, 29 and then to the pump, 26. The volume of the filter element and connecting pipe, 32, to the detector is kept small so that the transit time from the filter to detector is less than one second. The pumping speed of the pump, 26 is controlled to ensure that the optimum flow through the filter element, 21, is achieved.

The filter element, 21, may be made of any appropriate material or materials and method of construction, but preferably is a good conductor that is also chemically inert at temperatures up to 300 degrees centigrade. In a preferred embodiment, the filter element, 21, ensures that particles as small as one micron are stopped within the filter. Sintering is a well known technique for making such microporous filtration elements, a commonly used material being sintered bronze. Bronze filters are available in various shapes, including discs and cylindrical forms, and may be gold plated in some cases. The filer element, 21, may also be made of stainless steel, whether woven, felted, pressed into sintered discs, or prepared in any other appropriate manner. In one embodiment, the filer element, 21, may be an aluminum filter made by compressing aluminum powder of controlled particle size in a die press.

The filer element, 21, is preferably, but not necessarily, no more than 2 or 3 mm thick, as greater thicknesses will tend to increase transport time through the filter.

Most of the sampled air passing down the inlet tube, 22 does not impact the surface of the filter element because of the blanketing effect of the dry air curtain, 25. However, particles and heavy molecules have greater momentum than the lighter air molecules and will penetrate further into the boundary layer of dry air and are drawn into the filter element together with the dry air. The sampled air flow, dry air flow, filter flow, and distance from the end of the inlet tube, 22, to the surface of the filter, 21, all influence the transmission of vapors, particles and unwanted light molecules such as the oxides of nitrogen and water vapor. In order to optimize the transmission of target vapors and particles, while largely eliminating unwanted water vapor and oxides of nitrogen, both pumps, 23 and 26 may be switched on and the following setup procedures adopted:

1 Set the sample flow at pump, 23, to a flowrate that ensures the largest particles of interest are carried along in the air stream and the sampling rate will provide a representative sample from the object under inspection. For example for a hand held sniffer, a flowrate of 1 to 2 litres per minute is typical. When testing hand carried airline bags in an automatic test station, 100 to 200 litres per minute will be required. Portal tests demand that the air close to the body is efficiently sampled in a few seconds, and prior art methods have been adopted which sample at rates in excess of 600 litres per minute.

2 Set the vacuum produced by pump, 26, to ensure a fast response is obtained to a target vapor source applied to the inlet, 22.

3 Set the dry air flow, F1 in FIG. 2, on control valve, 27, to a level that largely eliminates the response to water vapor in the detector.

4 Adjust the distance from the sample inlet, 22, to the filter, 21, until the response to the lightest target vapor, e.g., ethylene glycol dinitrate, is just obtained.

These parameters are interdependent and an iterative process may be required in order to reach the optimum settings. Once the flowrates and parameters have been set, no further adjustment is required.

In a practical system such as is shown in FIG. 2, a dopant vapor may be required to provide ionic charge moderation as described in U.S. Pat. No. 5,491,337. A small flow of dry air is conveniently provided through a dopant chamber, 28, where vapor diffusing from a diffusion capsule is carried into the air entering the detector, 29. Also, it may be preferable to supply a flow of dry air down the drift tube of the detector at the opposite end of the detector from the sample inlet. This may be controlled such as is shown in FIG. 2 with a control valve, 29. The flowrate of the drift gas may be monitored such as by flowmeter, F3. All three dry gas flows can be conveniently provided by passing the effluent of the pump, 26, through a drying system, 30. This may be a simple tube packed with drying material such as molecular sieve, or alternatively any other automatic drying system may be employed, such as that described in U.S. Pat. No. 6,642,513, and shown in FIG. 3. The system of FIG. 3 has two drying tubes, A and B, one of which is hot and purging to atmosphere while the other is drying the gas supply to the apparatus. The two tubes are caused to alternate between drying and purging, thus maintaining a continuous supply of clean dry air to the apparatus.

Figure 2:
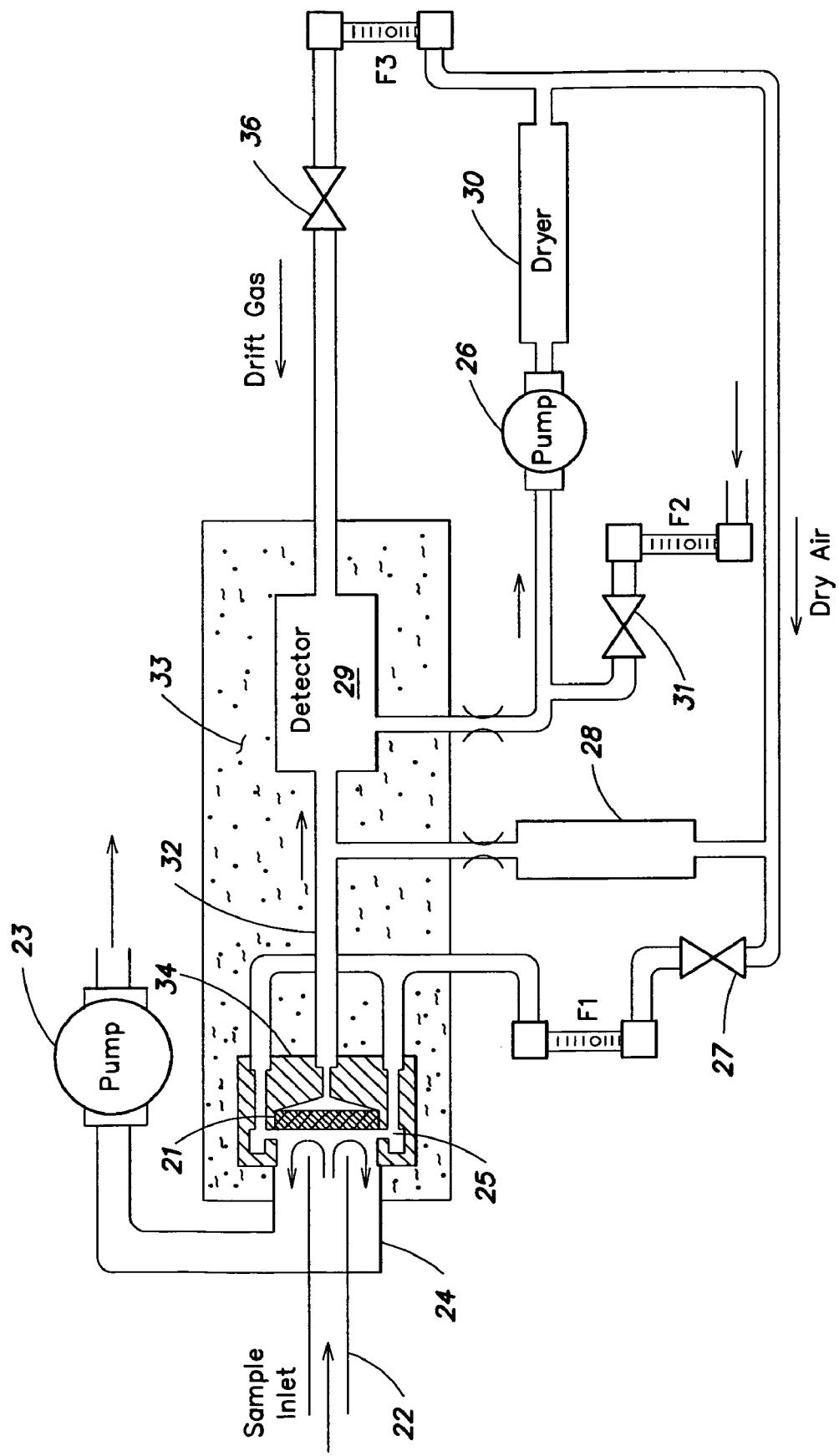

Much of the dried air is exhausted to atmosphere at the front of the filter element, 21, shown in FIG. 2. A make up airflow intake, F2 is provided at the vacuum side of the pump, 26 and is controlled either by a flow restriction, or valve, 31. The make up air stream is likely to be greater than the flow F1 injected into the front of the filter element when an automatic dryer system is in use, since some air is also exhausted through the dryer tube being purged to atmosphere.

In operation, air around or within the test object may be sampled by directing the inlet nozzle to the proximity of the threat. Contraband materials such as explosives and illicit drugs emit extremely low levels of vapor, and may release micro particles into the atmosphere, particularly if stimulated such as by vibration. Any particles and vapor entrained in the sample air stream entering the detection system impact the filter element due to their higher momentum than the incoming air stream. The filter may be maintained at an elevated temperature between 150 and 300 degrees Celsius to allow transmission of the low volatility target vapors, and to rapidly evaporate any particles. It is preferable to make the filter element of high thermal conductivity material such as sintered aluminum or bronze. This ensures that the filter will remain at a high temperature even when a cool stream of air is directed at it. The dry air curtain may be pre heated in the housing, 34, shown in FIG. 2, and also may act to maintain the filter at the elevated temperature. Target molecules that are drawn through the filter are carried into the detector through a short heated tube, 32. The filter housing, connecting tube and detector may all be maintained at elevated temperature and insulated by thermal insulation material, 33.

The preferred mode of operation allows for sample to be acquired, and then the pump, 23, to be shut off. This has several advantages in that continuous sampling tends to clog the filter, 21, and also reduces the filter temperature. Low filter temperature causes poor transmission of sample, and slows clear down after material is detected. The intermittent mode of operation further reduces the total amount of water vapor entering the detector. It also allows the response from particles and vapors to be differentiated. Particulate response clears down much more slowly than a vapor response after the pump is switched off. This is easily recognized by the operator, but can also be automatically determined by a software algorithm operating on the detector signal.

DETAILED DESCRIPTION OF PREFERRED EMBODIMENT FOR PORTAL DETECTION, AND AUTOMATIC BAGGAGE INSPECTION

The detection of vapor and particle emissions from the whole body of a person generally requires sample flows of approximately 10 to 30 litres per second in order to complete the test in a few seconds. Such flow would require sampling tube diameters of approximately 50 to 90 mm in order not to cause a high vacuum at the filter element. High vacuum levels cannot be tolerated, however, since the detector itself has to be operated below the inlet filter pressure, but near to atmospheric pressure, and this is problematic. The maintenance of an efficient dry air curtain across diameters of 50 to 90 mm is also extremely difficult. Furthermore, it becomes impossible to maintain the temperature across a large filter element when heating by conduction from the periphery.

In order to overcome these problems, a preferred embodiment for portal and automatic baggage configuration has been devised. This incorporates a multiplicity of smaller filter elements arranged in an array in a manifold system. The incoming sampled air stream is directed down several parallel tubes, 41, shown in FIG. 4. In the example illustrated, an array of seven parallel tubes is shown arranged in line with an array of seven filter elements acting as sample impacters as described in the detailed description of the preferred embodiment for low sample flows. It should be understood that other numbers of tubes and tube arrangements may also be employed.

Figure 5:
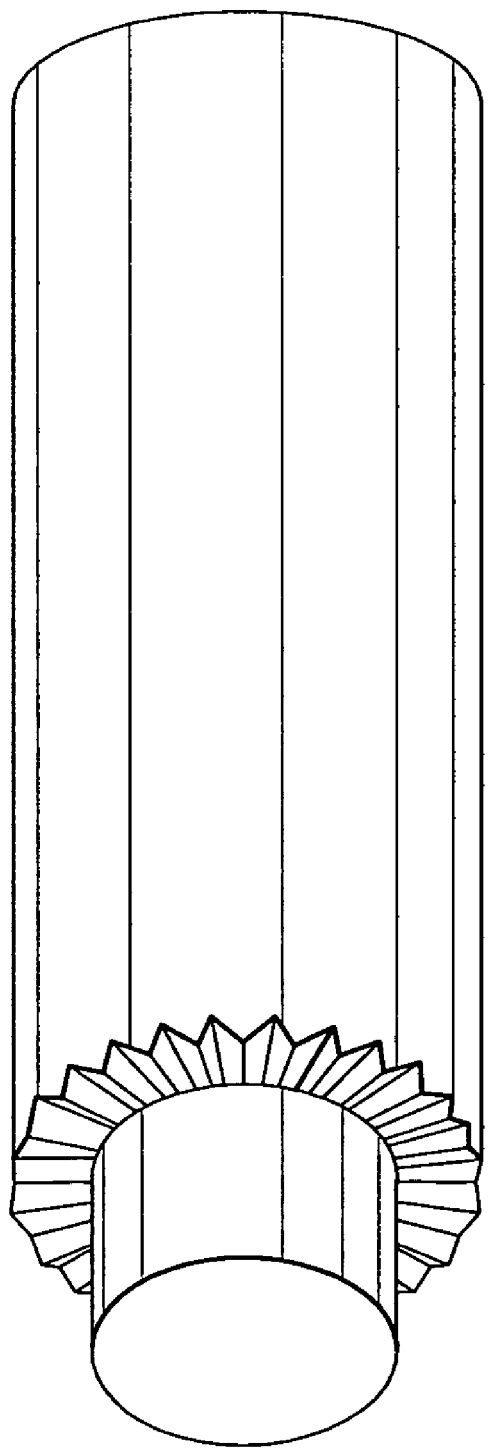

In this embodiment, a curtain of dry air is generated in front of each filter element in the same way as described in the previous section, but a novel means of providing a multiplicity of air curtains has been devised. The housing for the filters is comprised in two parts, shown in section in FIG. 4. The filters, 42, are held in cylindrical wells in the housing, 43, and a cover plate, 44, is attached to hold the filters in place and to provide an air curtain across each filter element. The filters and holes in the cover plate are arranged in line with the incoming sampled air streams, and around each hole in the cover plate, a radial array of grooves, 45, is engineered to provide an air curtain from an array of paths, 46, in the housing, 43. The radial grooves, may be conveniently stamped into the surface of the cover plate, 44, in a stamping process using a tool similar to that illustrated in FIG. 5. The stamping process is made easier if the housing and cover plate is made of brass or aluminum. The dry air paths, 46 may be conveniently milled in the surface of the housing 43 and dry air supply is connected into these from the back of the housing. It is preferable to supply the dry air from a number of supply points, 47 as shown, so that each ring has the same air pressure, and all air curtains are equal.

Air is drawn through each filter element, as previously described, and each effluent is connected together as shown in the pathways, 48, in FIG. 4. This is then piped to the detector through the heated pipe, 49. The flow through each filter element is substantially identical and is controlled by the pressure drop across the filter as described previously. The flowrate is controlled to provide a sample transit time of less than one second into the detector.

Figure 6:
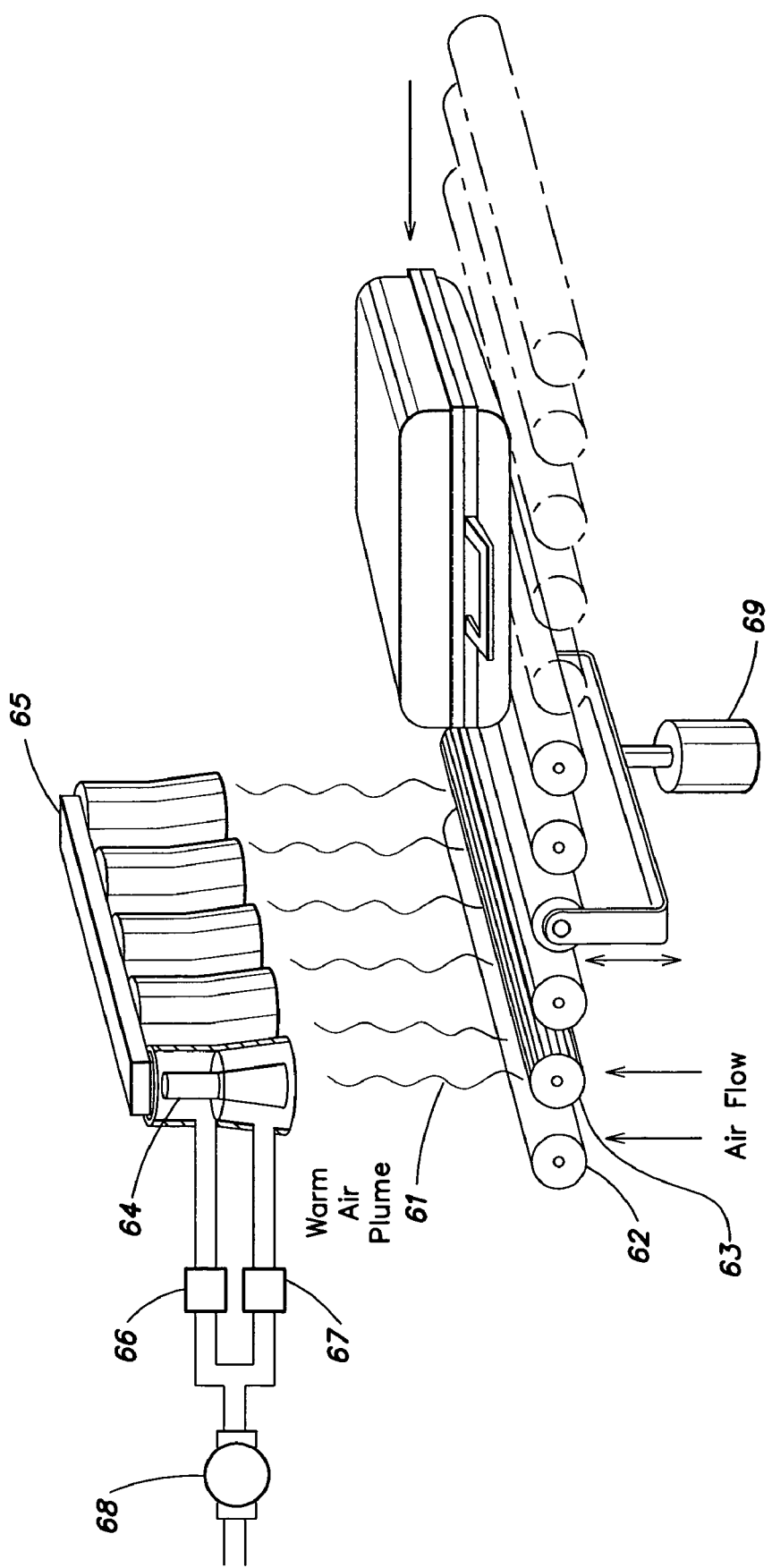

An automatic inspection station for the detection of traces of contraband in airline bags is shown in FIG. 6. The bags are conveyed through a test area that is enclosed on four sides with openings at front and back to allow transport of the bags. The conveyor is preferably made from number of independent rollers, 62, shown in FIG. 6, although other types of conveyers, such as open mesh designs, may also be employed.

In the roller embodiment, the rollers are driven at a controlled speed that ensures the trace detection cycle is complete before the bag emerges from the test station. A warm air plume is created from a heating element, 63, arranged in the tunnel below the rollers or, preferably, within one of the rollers so that the roller itself is heated. The air passes through the gaps adjacent the heated roller, is heated, and rises upwards to the sample inlets, 64.

The sample inlets may be a multiplicity of tubes as described above and shown in FIG. 4, but the preferred embodiment has an array of sample inlet tubes in parallel across the conveyor as shown in a cut-away view in FIG. 6. This allows the warm air plume generated across the conveyor to rise substantially vertically into the sample inlets. The sampled air impacts the filter elements in a manifold, 65, is then drawn into a pump, 68, through one of two valves, 66, and 67, at substantially the same flow as the warm air plume.

When no bag is in the test area, the sample air stream is caused to bypass the detector inlets by opening the valve, 67, and closing valve 66. By this means, the warm air plume is maintained at all times, but the filter elements in the sample inlet system do not become blocked. When a bag enters the test area it is detected by a suitable sensor, such as an optical beam sensor, the valve 67 is closed and the valve 66 is opened.

It is also advantageous to provide a vibration means, 69 either on a roller or under the conveyor at a position prior to the warm air plume. The vibration causes the bottom of the bag in contact with the vibrating roller to lift up and down repeatedly as the bag passes over the roller. This in turn causes the bag to ventilate air from inside the bag into the warm air stream. A frequency of 5 to 20 cycles per second is chosen to provide the optimum ventilation rate from typical hand carried and checked bags. It may also cause particles adhering to the outside of the bag to be dislodged and these too are carried by the warm air stream into the detection system.

In a preferred embodiment, the inlet flow that is drawn into the detection system is arranged to be approximately equal to the warm air stream induced by the heater, 63. This provides the least dilution or loss of sample that may be carried in the warm air stream. Large bags do interrupt the warm air plume, but the airflow around the periphery of the bag increases to maintain a substantially constant flow rising toward the detector inlet. Most of the air is ventilated from bags at the periphery of the bag, or from the seam between the two halves of a typical suitcase. It is preferable to place all bags so that they are laid flat (i.e., smallest dimension upwards, as shown in FIG. 6) on the conveyor in the same way as is required for x-ray inspection of the bags. This facilitates the pumping of a bag and the ventilated air is carried directly into the air plume.

In one embodiment of the subject invention, the x-ray inspection and the trace detection station is combined in the same tunnel. This allows the bags to be searched for weapons and contraband materials by the integrated test station.

Figure 7:
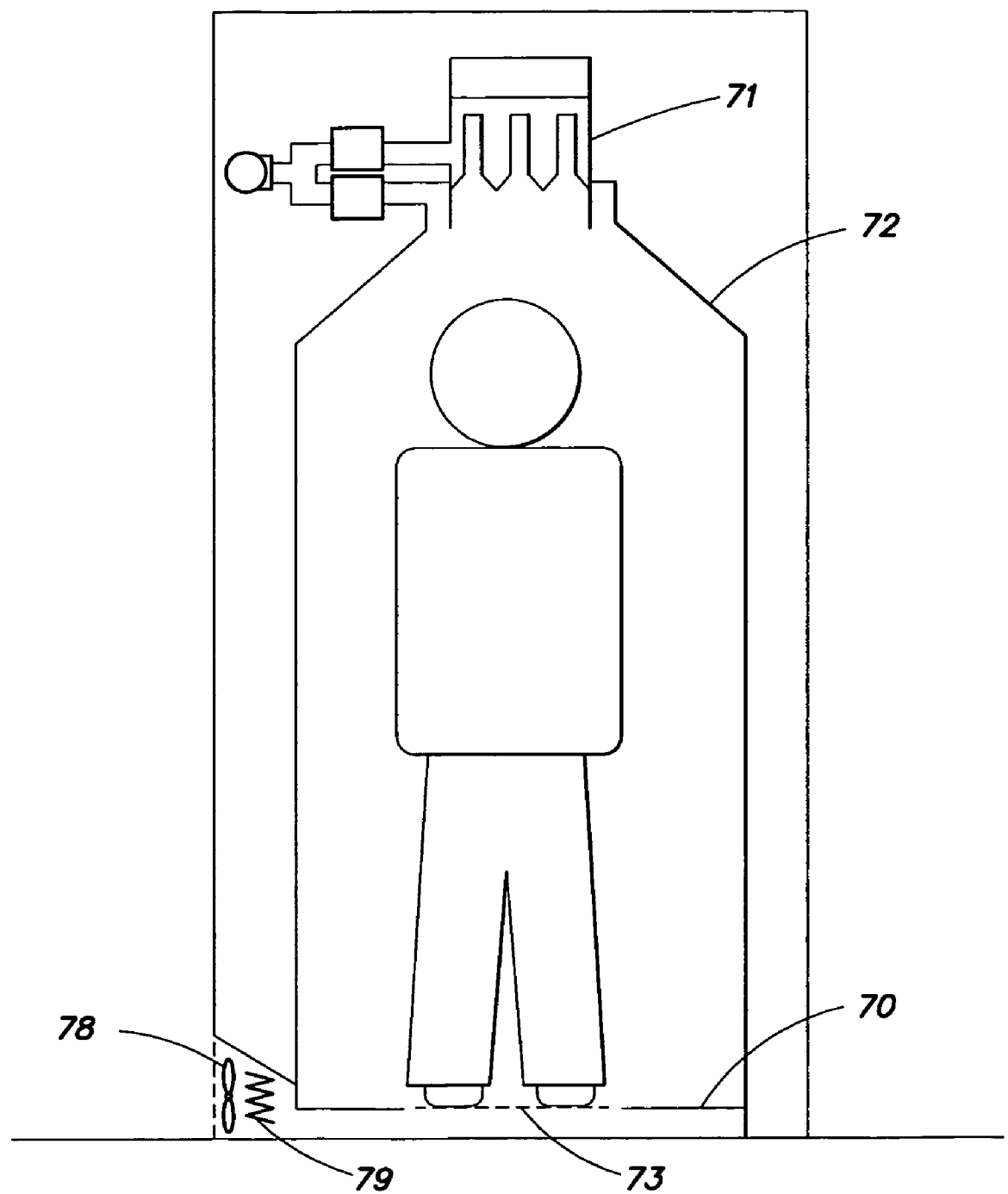

A preferred embodiment for portal detection of contraband is shown in FIG. 7. The detection system was described earlier in reference to FIG. 4. The sample inlets, 41, shown in FIG. 4, are connected into a short tube, 71, of approximately 100 mm diameter, whose inlet is arranged about two meters above the floor of the portal, 70. A concentric tube, 72, approximately 150 mm diameter is mounted around the sample inlet tube, 71, and acts as a bypass flow path to direct the sampled air away from the detection system interface when no subject is in the portal. Electrically or pneumatically operated gate valves, 76 and 77, control the direction of the air stream. When valve 77 is open, valve 76 is closed and the air stream bypasses the filter elements described earlier. When a subject enters the portal, the valve 77 is closed and valve 76 is opened, thus allowing the air passing over the subject to be sampled into the detection system.

A warm air plume may be generated within the portal from a heating element in the floor of the portal. It is better to avoid a step-up into the portal, but the warm air stream is preferably generated below the feet in order to sample the whole body. In the preferred embodiment, a fan, 78, and small heater, 79, is arranged in the wall of the portal and the outlet is ducted into a small gap between the portal floor and the surrounding floor level. The center of the portal floor has an open grill, 73, which allows the warm air to escape into the portal. This provides the initial airflow to form the warm air plume.

The grill, 73, is preferably caused to vibrate at sonic or ultrasonic frequency, but not at an amplitude which would cause discomfort to the person under test. This has the effect of dislodging some particles that may be adhering to the outside of clothing of a subject standing on the grill. The vibration causes particles within the test subject's clothing to migrate to the outside, and air within the clothing to ventilate, thus carrying any contraband particles and vapors into the warm air plume and on to the detector. A ramp may be provided at the entrance and exit from the portal, so that no step is necessary into the portal, and wheelchairs may access the portal.

In operation, the subject is sensed on entering the portal, optically, by weight, or otherwise, and will be directed, such as a traffic control signal or an exit door, to remain within the portal until the test is complete. Contraband sample vapors and particles released into the warm air plume are quickly carried into the detection system where they are detected. Total test time is preferably between 3 and 6 seconds, but clear down from a positive response may take longer. If no contraband is detected, the subject is allowed to continue through the portal.

It may be convenient to carry out other known inspection processes at the same time as the contraband test is made. Weapons detection either by metal detection, x-ray, or terahertz scanning can be combined with the trace contraband test. Similarly, ionizing radiation monitors can be mounted in the portal to provide detection of nuclear threat materials. The signals from all the detection processes can be integrated to provide an automatic inspection portal for chemical contraband, weapons and nuclear threat materials.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

The invention claimed is:

1. A detector for the detection for trace vapors and particles in the air comprising:

a housing;

at least one well formed in the housing, the well having an open end and a closed end;

a heated filter positioned across the open end of the at least one well;

a sampled air source delivering sampled air substantially perpendicular to the open end of the at least one well on a first side of the filter;

a dry air source to supply dry air across the first side of the filter at a first pressure;

a detector line in communication with the at least one well on a second side of the filter; and a second dry air source for supplying air to a second side of the filter opposite the first side at a second pressure lower than the first pressure.

2. The detector of claim 1, further comprising a cover plate positioned on the side of the housing containing the well.

3. The detector of claim 2, wherein the cover plate includes at least one channel constructed and arranged to deliver the dry air to the first side of the filter.

4. The detector of claim 3, wherein the channels are arranged radially.

5. The detector of claim 1, wherein the detector line is heated.

6. The detector of claim 1, wherein the filter is made of one of sintered bronze, aluminum, and stainless steel.

7. The detector of claim 1, wherein the filter is made of gold-plated ceramic.

8. The detector of claim 1, wherein the filter is constructed and arranged to stop particles as small as 1 micron in diameter.

9. The detector of claim 1, wherein a pressure differential across the filter provides a flow through the filter that is insufficient to eliminate a dry air boundary layer at the first side of the filter.

10. A method for the detection for trace vapors and particles in air, the method comprising the steps of:

drawing sampled air against a heated filter to create a substantially stagnant boundary layer against the surface of the filter;

introducing dry air into the boundary layer;

creating reduced pressure at the second side of the filter sufficient to induce a small air flow through the filter but insufficient to eliminate the boundary layer of dry air at the first side of the filter; and drawing the air that has passed through the filter into a detector.

11. The method of claim 10, wherein the filter is heated to between about 150 and 300 degrees Celsius.

* * * * *